United States Patent [19]
Frazee et al.

[11] Patent Number: 5,062,848
[45] Date of Patent: Nov. 5, 1991

[54] HEMOSTATIC CLIP AND APPLICATOR THEREFOR

[76] Inventors: John G. Frazee, 17357 Magnolia, Encino, Calif. 91316; Roger J. Malcolm, 920-C Calle Negocio, San Clemente, Calif. 92672

[21] Appl. No.: 680,107

[22] Filed: Mar. 26, 1991

Related U.S. Application Data

[62] Division of Ser. No. 489,900, Mar. 7, 1990, Pat. No. 5,032,127.

[51] Int. Cl.$^5$ ............................................. A61B 17/00
[52] U.S. Cl. .................................. 606/213; 606/157; 227/902
[58] Field of Search ............... 606/157, 158, 213, 221; 227/902

[56] References Cited

U.S. PATENT DOCUMENTS

| | | | |
|---|---|---|---|
| 3,601,127 | 8/1971 | Finegold | 606/157 |
| 4,217,902 | 8/1980 | March | 606/157 |
| 4,337,774 | 7/1982 | Perlin | 606/158 |
| 4,390,019 | 6/1983 | Leveen et al. | 606/158 |
| 4,796,627 | 1/1989 | Tucker | 606/157 |
| 4,832,027 | 5/1989 | Utz | 606/157 |

*Primary Examiner*—Stephen C. Pellegrino
*Assistant Examiner*—Gary Jackson
*Attorney, Agent, or Firm*—Peter L. Klempay

[57] ABSTRACT

A hemostatic clip which permits selection of the clamping pressure applied by the clip to tissue is of single piece plastic construction and C-shaped configuration. A transversely extending region of reduced thickness at the center of the mid-portion of the clip defines the hinge axis of the clip. Cooperating latching members extend from the mid-portion on opposite sides of the reduced thickness region. A dispenser for the clips has a magazine for storing a series of clips, a dispensing mechanism for advancing clips from the magazine, and an applicator tip receiving the advanced clip and having adjustably spaced plates for determining the degree to which the clip is closed.

12 Claims, 4 Drawing Sheets

HEMOSTATIC CLIP AND APPLICATOR THEREFOR

The present invention pertains to hemostatic clips and to tools for applying such clips.

BACKGROUND OF THE INVENTION

Hemostatic clips are used during surgical procedures to control bleeding along the edges of the incision, the clips being applied to the tissue with sufficient clamping force as to close off the blood vessels therein. The clamping pressure must be limited, however, so as to avoid permanent injury to the skin or other tissue and the limiting pressure varies from patient to patient, lower pressure limits being necessary for pediatric than for adult patients, for example. It is also necessary that the clips be readily removable at the end of the procedure.

The clips may be applied using a forceps-like device. However, such devices are capable of applying only a single clip at a time, unduly slowing the process. A number of hemostatic clip applicators which are capable of holding a number of clips and of applying the clips in succession have been devised. Examples of such applicators are disclosed in U.S. Pat. No. 4,557,263, Green; U.S. Pat. No. 4,612,932, Casper et al.; U.S. Pat. No. 4,624,254, McGarry et al.; U.S. Pat. No. 4,637,395, Casper et al.; U.S. Pat. No. 4,646,740, Peters et al.; U.S. Pat. No. 4,671,278, Chin; and U.S. Pat. No. 4,712,549, Peters et al. The relative complexity of these devices is a limiting facture in their use.

It is a primary object of the present invention to provide a hemostatic clip which may be applied with facility and which provides a selected level of clamping pressure.

It is also an object of the present invention to provide such a hemostatic clip which is readily removable.

A further object of the invention is the provision of a tool for applying such clips in rapid succession.

SUMMARY OF THE INVENTION

The above and other objects of the invention which will become apparent hereinafter are achieved by the provision of a hemostatic clip consisting of a single-piece molded plastic member of flattened C-shape configuration having facing jaws of mating configuration, ie.g., sinusoidal, the mid-portion of the clip distal to the jaws being of reduced thickness to function as a hinge; and a pair of tabs connected to the mid-portion on opposite sides of the hinge region, extending in overlapping relation to one another and provided with a series of detents. Successive ones of the clips may be interconnected by integral webs to form a chain of clips.

The clip applicator tool includes a magazine for storage of a plurality of the clips; a passage extending from the magazine and terminating in an applicator tip, the passage serving to feed successive clips to the applicator tip, the applicator tip including a pair of guide rails positioned to engage opposite sides of the clip to force the clip into a clamping relation with the skin or other tissue, the separation of the guide rails preferrably being adjustable to vary the clip clamping pressure; and an actuating mechanism for driving the clip into and through the guide rails. The actuating mechanism may also serve to sever the clip connecting webs.

For a more complete understanding of the invention and the objects and advantages thereof, reference should be had to the accompanying drawings and the following detailed description wherein preferred embodiments of the invention are illustrated and described.

DESCRIPTION OF THE PREFERRED EMBODIMENTS

Figure 1:
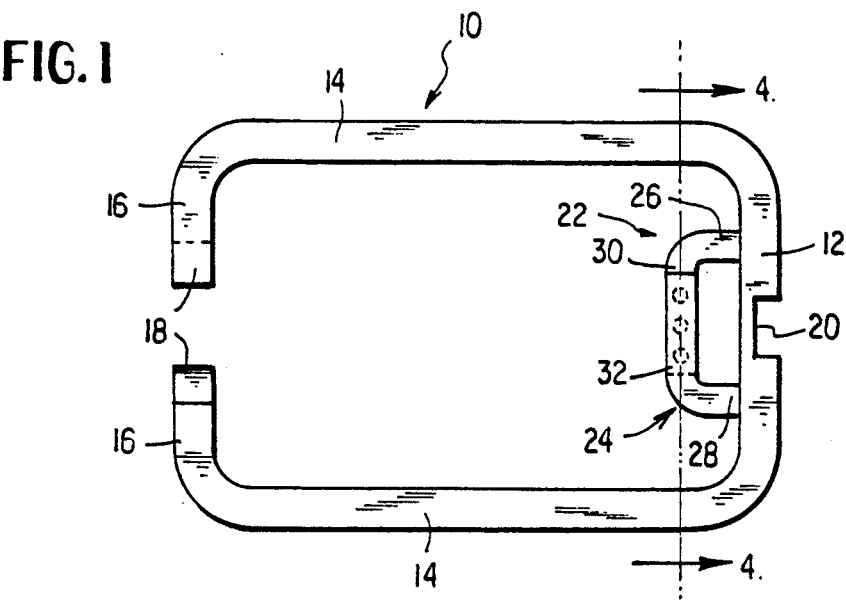
FIG. 1 is a side elevational view of a first embodiment of the hemostatic clip of the present invention.
Figure 2:
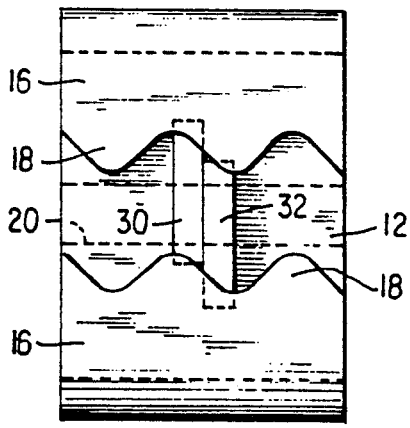
FIGS. 2 and 3 are front and rear elevational views, respectively, of the clip of FIG. 1.
Figure 3:
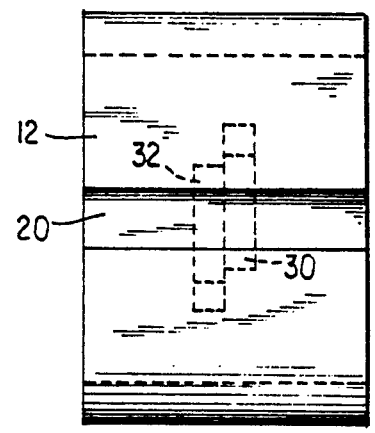
Figure 4:
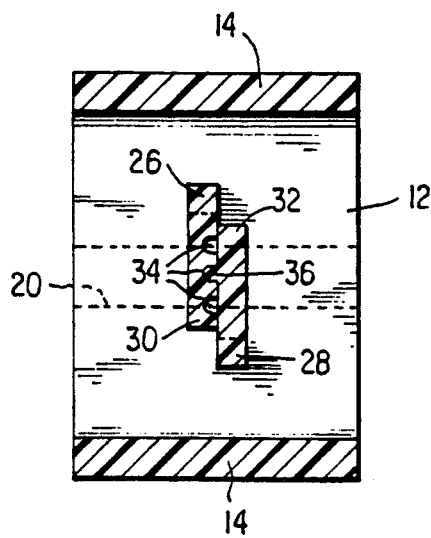
FIG. 4 is a cross sectional view taken on the line 4—4 of FIG. 1.

Referring first to FIGS. 1-4, a first embodiment of the hemostatic clip of the present invention, designated generally by the reference numeral 10, will now be described. The clip 10 is of single piece molded plastic construction having, in profile, a C-shaped configuration having a mid-portion 12, a pair of arms 14 extending therefrom and, at the free end of each arm, a jaw 16. As is shown in FIG. 2, the jaws extend toward one another with their respective mating edges 18 being of complementary sinusodial configuration. A groove 20 extends transversely across the outer side of the mid-portion of the clip at the center thereof, forming a reduced thickness region functioning as a hinge. On the inner side of the clip mid-portion and symmetric about the midpoint thereof are provided a pair of inwardly projecting tabs 22, 24. Each tab includes a base portion 26, 28 connecting the tab to the mid-portion 12 and a head portion 30, 32, the head portions extending in overlapping relation to one another and with the adjacent faces thereof in sliding contact. The adjacent face of one of the tab head portions has a series of indentations 34 spaced along an arc centered at the hinge point of the mid-portion 12 and the corresponding face of the other tab has a laterally extending projection 36 in alignment with the arc of indentations.

The clip 10 is applied to the skin or other tissue by positioning it on the tissue with the two jaws 16 on opposite sides thereof. When the clip is located at the desired position, pressure is applied to the arms 14 to force the jaws 16 toward one another, the clip bending about the hinge region defined by the groove 20, and apply clamping force to the tissue. The indentations 34 and projection 36 of the tabs serve to retain the clip at the desired level of clamping pressure. The clip may be removed by severing the mid-portion at the groove 20.

Figure 5:
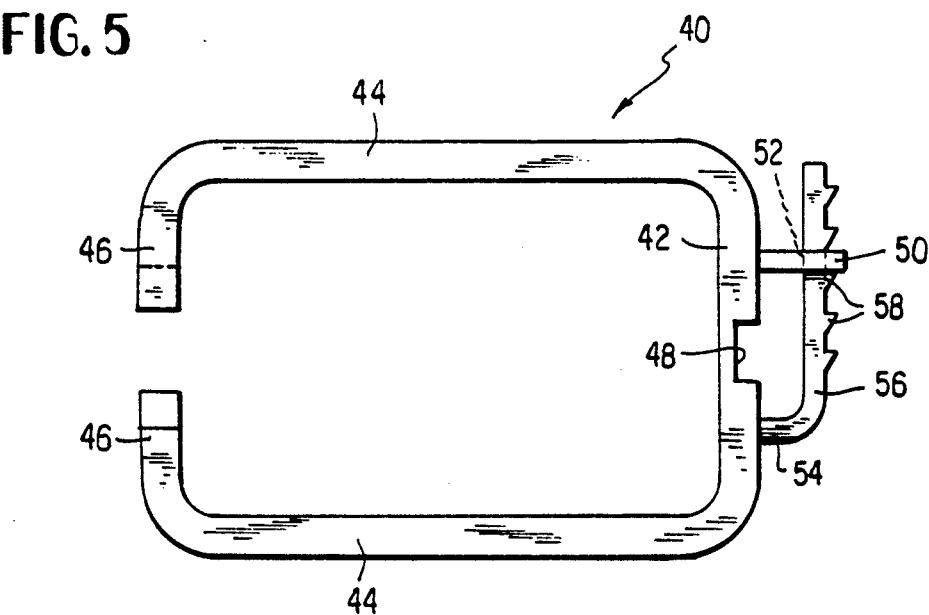
FIG. 5 is a side elevational view of a second embodiment of the hemostatic clip of the present invention.
Figure 6:
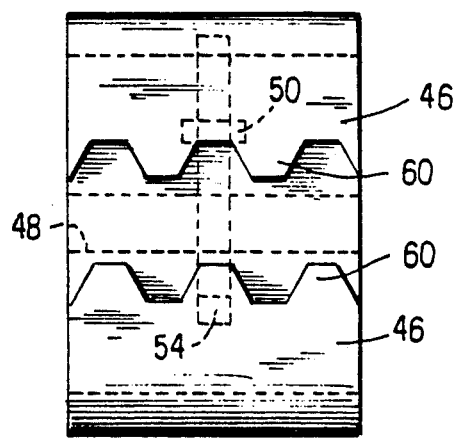
FIGS. 6 and 7 are front and rear elevational views, respectively, of the clip of FIG. 5.
Figure 7:
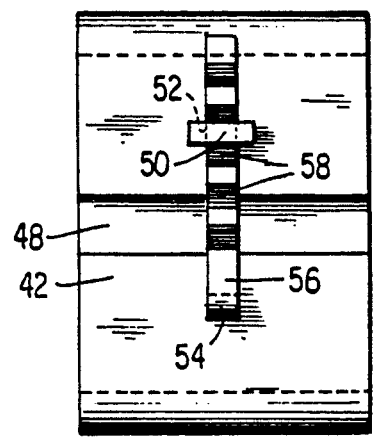

A modification of the hemostatic clip is illustrated in FIGS. 5-7. This embodiment of the clip, designated generally by the numeral 40, differs from that described above in that the clamping pressure retention means, corresponding to the interengaging tabs 22, 24 of the previously described embodiment, is located externally of the throat of the clip, thereby allowing a greater throat depth. This embodiment of the clip is, again, of C-shaped configuration, having a mid-portion 42, a pair of arms 44 extending therefrom and jaws 46. A groove 46 extends transversely across the mid-portion at the center thereof, forming a reduced thickness region functioning as a hinge. Projecting outwardly from the mid-portion on one side of the groove is a first lug 50 having a through opening 52. A second lug 54 projects outwardly from the mid-portion on the opposite side of the groove and includes an elongated end portion 56 extending generally parallel to the mid-portion and through the opening 52 and provided on its outer face with a series of ratchet teeth 58.

As the clip 40 is compressed into clamping relation on the tissue, the end portion 56 of the lug 54 moves through the opening 52 of the lug 50. Reverse movement of the clip arms in the unclamping direction is prevented by the engagement of one of the ratchet teeth 58 with the lower face of the lug 50. Severing of the clip mid-portion at the groove 50 may be employed to remove the clip.

A modified form of the clip jaws is shown in FIG. 6. In this embodiment, the mating edges of the jaws 46 are provided with teeth 60 of generally triangular or saw tooth configuration. Such an arrangement is preferably when penetration of the tissue is desired.

Figure 8:
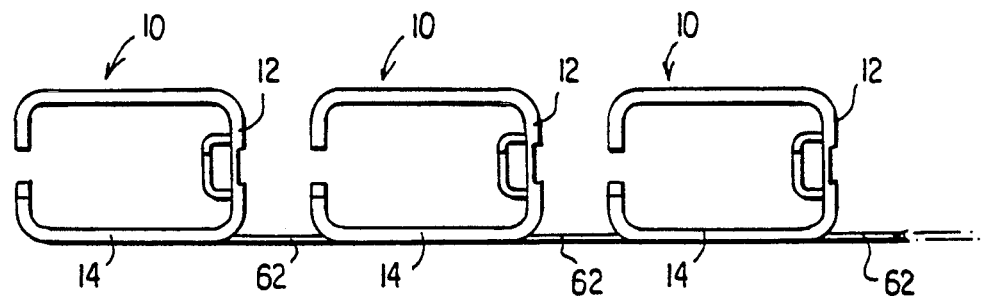
FIG. 8 is a side elevational view of a chain of interconnected hemostatic clips.

The hemostatic clips of either embodiment may be formed as individual units or, as illustrated in FIG. 8, in a chain of clips. In the latter configuration, a thin web or strap 62 joins the mid-portion 12 of each clip to the forward end of one leg 12 of the adjacent clip. This arrangement is preferrable when the clips are to be applied with the use of an applicator tool.

A clip applicator tool 70 is illustrated in FIGS. 9-14. The tool includes a base plate 72 having a handle portion 74 projecting therefrom, a detachable magazine 76 for holding a supply of hemostatic clips, a clip dispensing mechanism 78, and a trigger 80 for actuating the mechanism.

The magazine is preferrably formed of transparent plastic and has spaced front and back walls 82, 84 joined by a side wall 86 and a partition wall 88 forming a spiral chamber for holding a series of clips An open ended exit passage 90 extends tangentially from the outermost turn of the chamber, the upper wall of the passage having an elongated opening 92. A through bore 94 is provided at the center of the magazine. The magazine may be a disposable item, intended to be discarded after dispensing the clips therefrom. To prevent misuse of such a disposable magazine, means may be provided in the magazine to prevent the refilling thereof. For example, a leaf spring 138 may be formed in one of the interior walls of the exit passage 90, the spring being oriented so as to permit movement of the clips toward the exit end of the passage but assuming a position, shown in dotted line, which precludes movement of clips inwardly after the final clip in the originally stored series has been dispensed.

Figure 13:
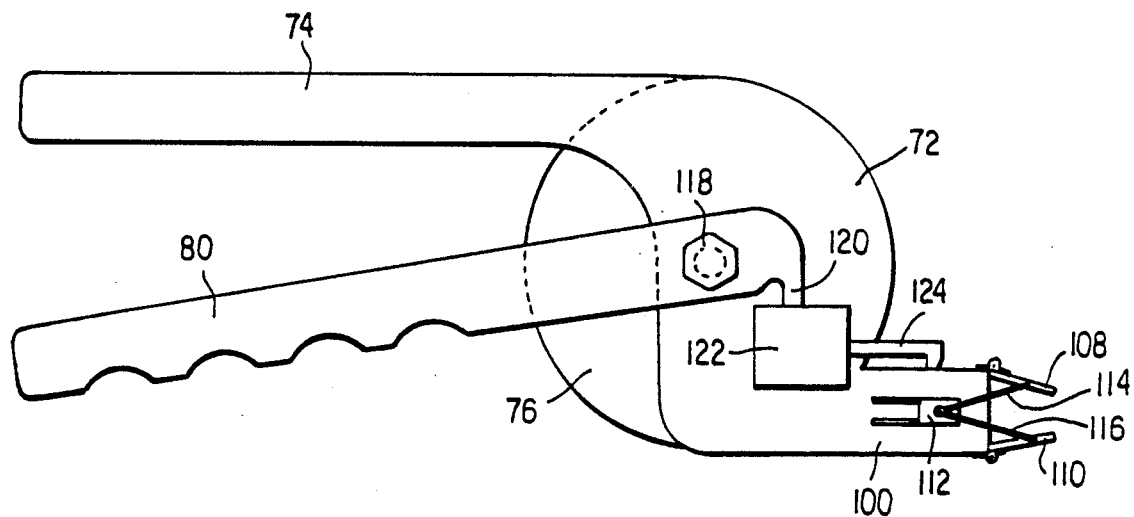
FIG. 13 is an elevational view of the clip applicator viewed from the opposite side from that shown in FIG. 9.
Figure 14:
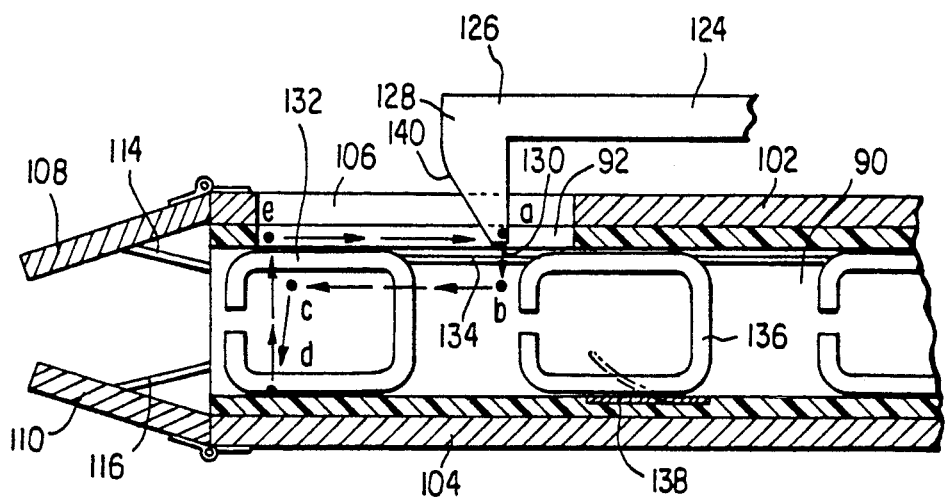
FIG. 14 is a diagrammic showing of the sequence of movement of the point of the clip dispensing pawl through a single clip applying cycle.

Attached to the base plate 72 is a stub shaft 96 which projects through the bore 94 of the magazine, a fastener 98 such as a clip or nut being received on the free end of the stub shaft to retain the magazine in place. The base plate 72 includes a lateral extension 100 in juxtaposition to the magazine exit passage 90, the extension having upper and lower flanges 102, 104 projecting across the upper and lower walls of the exit passage to retain the magazine in fixed position on the base plate, the upper flange having an elongated opening 106 in alignment with the opening 92 of the corresponding exit passage wall. The flanges terminate in alignment with the outer end of the passage 90. A pair of guide rails or plates 108, 110 are pivotally connected to the upper and lower flanges, respectively, forming an extension of the flanges which functions as the clip applicator tip. An adjustment mechanism is provided for moving the plates in unison toward or away from each other, as indicated by arrows in FIG. 9, to adjust the height of the exit end of the applicator tip and, accordingly, the degree to which a clip will be closed upon discharge therethrough. One type of adjustment mechanism is shown in FIG. 13 and consists of a slide member 112 carried on the rear face of the base plate extension 100 and a pair of links 114, 116 attached at one end to the slide member and, at their opposite ends, to the respective plates 108, 110 adjacent the outer ends thereof.

Figure 9:
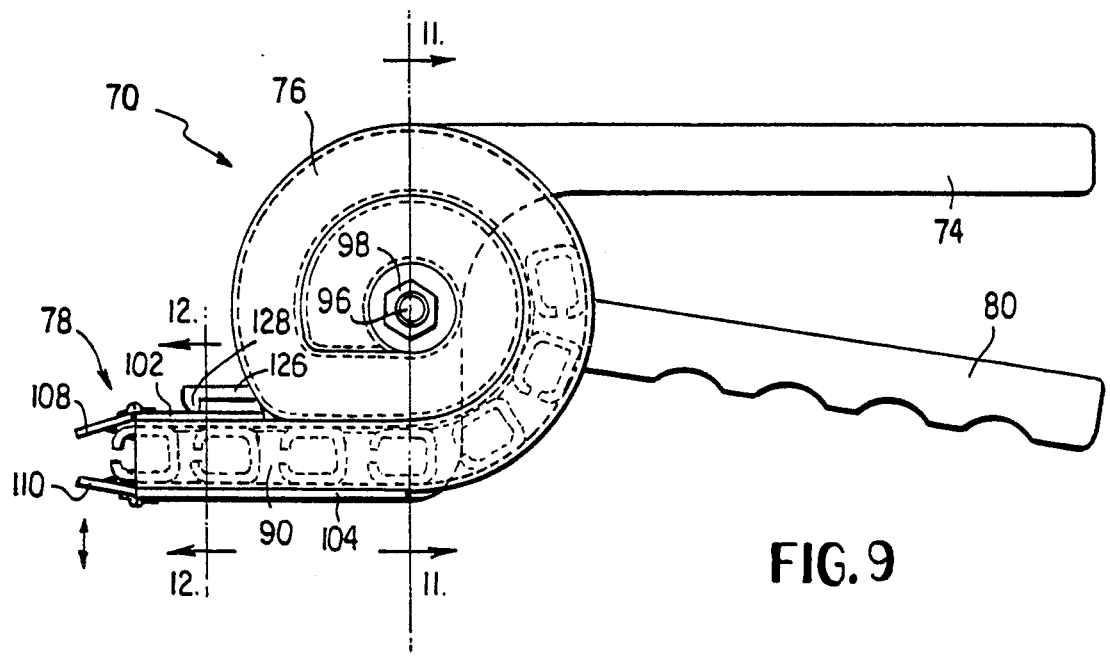
FIG. 9 is a side elevational view of the clip applicator tool of the present invention.
Figure 10:
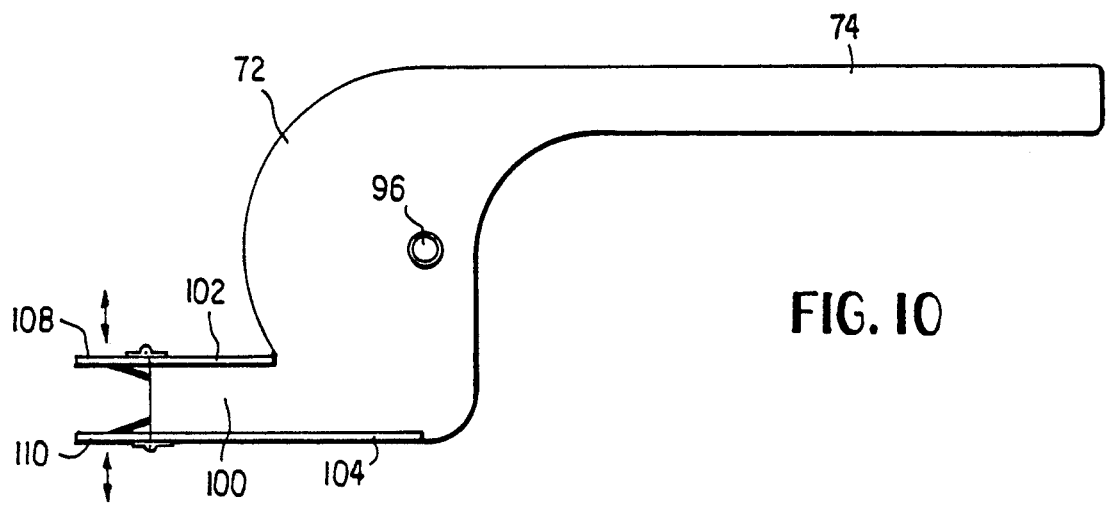
FIG. 10 is a side elevational view of the base plate of the applicator.
Figure 12:
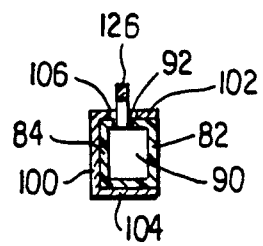
FIGS. 11 and 12 are transverse cross sectional views taken on the lines 11—11 and 12—12, respectively, of FIG. 9.
Figure 11:
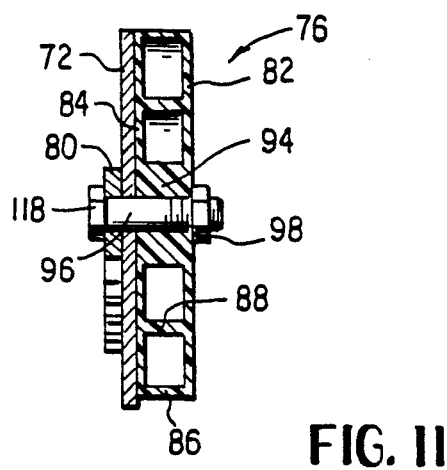

The trigger 80 is carried by a rearward extension 118 of the stub shaft 96 affixed to the base plate, the trigger pivoting about the extension and being spring loaded to normally assume the release position shown in FIG. 9. A downwardly projecting arm 120 of the trigger connects to a camming mechanism 122 which, in turn, moves a dispensing lever 124 the forward end 126 of which is provided with a downwardly projecting pawl 128. When the trigger arm is in the release position, the tip 130 of the pawl projects through the slot 106 of the upper flange 102 and into the slot 92 of the magazine exit passage 90 to a point a above and adjacent to the upper rear corner of the leading clip 132. As the trigger arm 80 is moved toward the handle 74, the projecting arm 120 moves into the camming mechanism 122 which serves to move the dispensing lever 124 so that the tip 130 moves into the exit passage to the point b at which the pawl 128 contacts the rear corner of the clip 132. As movement of the trigger arm toward the handle continues, the pawl tip advances to point c, forcing the leading clip between the applicator tip plates 108, 110. During this portion of the dispensing cycle, the leading clip 132 remains connected, by the web 134, to the next clip 136 so that movement of the pawl tip from b to c also serves to advance the next clip 136 and each of the remaining clips in the magazine. From point c, the pawl tip moves inwardly to point d, severing the connecting web 134 while the inclined forward edge 136 of the pawl forces the leading clip 132 further through the applicator tip, bringing the jaws of the clip into clamping engagement with the tissue edges. Upon initiation of movement of the trigger toward the release position, the pawl tip retracts to point e clear of the path of movement of the clips through the exit passage. With continued movement of the trigger in the release direction, the pawl tip returns to point a.

While preferred embodiments of the invention have been illustrated and described in detail herein, it will be apparent that changes and additions may be had therein and thereto without departing from the spirit of the invention. Reference should, accordingly, be had to the appended claims in determining the true scope of the invention.

We claim:

1. A hemostatic clip comprising:
a single-piece molded plastic member of generally C-shaped configuration having a pair of arms; a jaw at the first end of each arm, said jaws extending toward one another and having mating facing edges; a mid-portion connecting the other ends of said arms, said mid-portion having a centrally located transverse region of reduced thickness extending thereacross and forming a hinge about which said arms and jaws pivot; and first and second cooperating latching members, said members having base portions extending from said mid-portion on opposite sides of said region, respectively, and head portions extending in overlapping relation to one another and provided with a series of interengaging means.

2. The hemostatic clip of claim 1 wherein said mating faces of said jaws are of sinusodial configuration.

3. The hemostatic clip of claim 1 wherein said mating faces of said jaws are of saw tooth configuration.

4. The hemostatic clip of claim 1 wherein said latching members are located on the side of the mid-portion from which said arms extend.

5. The hemostatic clip of claim 4 wherein said mating faces of said jaws are of sinusodial configuration.

6. The hemostatic clip of claim 4 wherein said mating faces of said jaws are of saw tooth configuration.

7. The hemostatic clip of claim 1 wherein said latching members are located on the side of the mid-portion opposite that from which said arms extend.

8. The hemostatic clip of claim 7 wherein said mating faces of said jaws are of sinusodial configuration.

9. The hemostatic clip of claim 7 wherein said mating faces of said jaws are of saw tooth configuration.

10. A hemostatic clip comprising:
a pair of arms;
a jaw at the first end of each arm, said jaws extending toward one another and having mating facing edges;
a mid-portion connecting the other ends of said arms, said mid-portion having hinge means extending transversely thereacross at the center thereof; and
first and second cooperating latching members, said members having base portions connected to and extending from said mid-portion on opposite sides of said hinge means and head portions extending in overlapping relation to one another and provided with a series of interengaging means.

11. The hemostatic clip of claim 10 wherein said latching members are located on the side of the mid-portion to which said arms are connected.

12. The hemostatic clip of claim 10 wherein said latching members are located on the side of the mid-portion opposite that to which said arms are connected.

* * * * *